United States Patent [19]

Toriello

[11] 3,976,078

[45] Aug. 24, 1976

[54] ACUPUNCTURE NEEDLE UNIT

[75] Inventor: Danti Toriello, Des Moines, Iowa

[73] Assignee: Meridian Corporation, Des Moines, Iowa

[22] Filed: Nov. 22, 1974

[21] Appl. No.: 526,322

Related U.S. Application Data

[63] Continuation-in-part of Ser. No. 432,995, Jan. 14, 1974, abandoned.

[52] U.S. Cl. .......................... 128/329 A; 16/110 R; 403/272

[51] Int. Cl.² ...................... A61B 17/34; B25G 3/34

[58] Field of Search ............ 128/329; 403/247, 272; 16/110 R

[56] References Cited

UNITED STATES PATENTS

| | | | |
|---|---|---|---|
| 2,157,918 | 5/1939 | Rankin | 403/272 X |
| 2,286,435 | 6/1942 | Nerney | 403/272 |
| 2,503,643 | 4/1950 | Verbrugge | 16/110 R X |
| 2,642,872 | 6/1953 | Parker | 128/329 |
| 3,861,392 | 1/1975 | Moen | 128/329 A |
| 3,875,944 | 4/1975 | Toyama | 128/329 A |

*Primary Examiner*—Channing L. Pace
*Attorney, Agent, or Firm*—Rudolph L. Lowell

[57] ABSTRACT

The needle unit is particularly adapted for use in acupuncture treatments and consists of a flexible needle member formed with a pointed end portion having an angle of about four degrees relative to the longitudinal axis of the needle. The angle is formed by axially advancing the needle transversely of the axis of a rotatable forming or grinding tool. A tubular handle member is mounted about the opposite end portion of the needle member with the outer end thereof substantially flush with the corresponding end face of the needle member. The handle member is rigidly secured to the needle member by the application of a silver solder about the needle at opposite ends of the handle member.

1 Claim, 9 Drawing Figures

ACUPUNCTURE NEEDLE UNIT

This application is a continuation-in-part of application Ser. No. 432,995, filed Jan. 14, 1974 now abandoned.

SUMMARY OF THE INVENTION

The acupuncture needle unit is comprised of only two members composed of a stainless steel material and relatively constructed for economical manufacture and assembly into an integral unit. The needle unit is adapted to be made in different lengths so it can be used to treat all body portions of patients, is readily sterilized, and is capable of being used efficiently over prolonged periods of use with a minimum of pain to a patient.

DETAILED DESCRIPTION OF THE INVENTION

Figure 1:
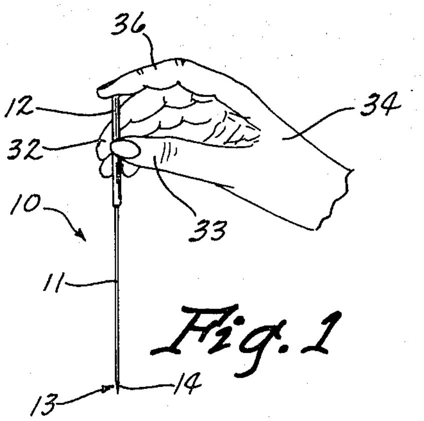
FIG. 1 shows the needle unit of this invention as held in the hand during an acupuncture treatment.
Figure 3:
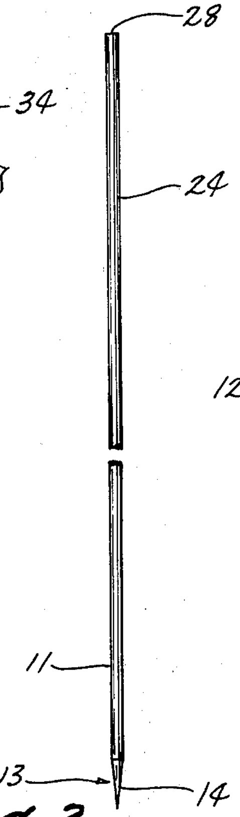
FIG. 3 is a foreshortened side elevational view of the needle member that forms part of the needle unit.
Figure 2:
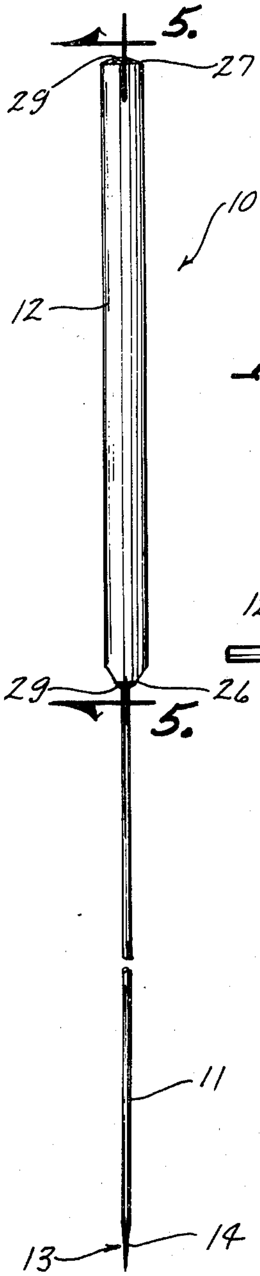
FIG. 2 is a foreshortened side elevational view of the needle unit.

The needle unit of this invention, indicated generally at 10 in FIGS. 1 and 2, is seen to include a needle member 11 equipped with a handle member 12.

The needle member 11 is elongated and flexible and composed of a stainless steel wire. The insertible or operating end 13 of the needle member has a terminal tapered or pointed section 14. This terminal section is formed by a grinding operation wherein the needle member 11 (FIG. 6) is advanced into a grinding engagement with a rotatable grinding tool 16 with the axis thereof in a plane normal to the axis of rotation of the grinding tool. The needle is guidably supported for axial movement within a bore 17 of a jig 18 that includes a supporting leg 19 adjustably mounted on the tool frame (not shown) to position the axis of the needle transversely of the axis of the grinding tool 16 such that the section 14 of the needle member 11 is acted upon only by a predetermined circumferential length of the grinding tool. This predetermined length thus functions as a die to form the needle point.

Figure 6:
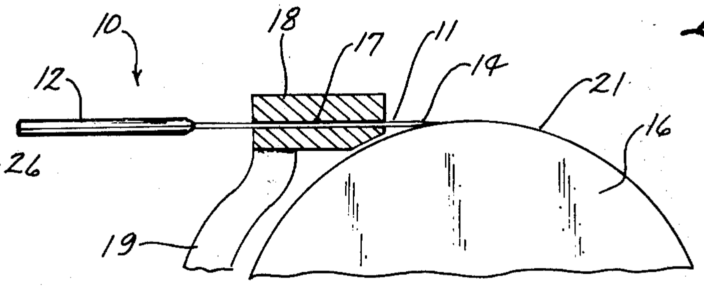
FIG. 6 is a diagrammatic showing of a grinding apparatus for forming the pointed end of the needle member.

As shown in FIG. 6, with a tool 16 having a 3 inch radius and the needle member 11 adjusted with its axis substantially tangent to the upper side of the tool 16, about one-eighth of an inch of needle is acted upon. The peripheral surface 21 of the tool 16 thus determines the taper of the needle point 14, so that the surface of the needle point axially of the needle member is of a minutely concave shape, as indicated at 22 in FIG. 8. This tapered shape is obtained by grasping the handle member 12 of the needle unit and then rotating and advancing the needle member 11 relative to the grinding tool 16. With the needle member positively guided within the bore 17 of the jig 18, the needle member 11 is accurately machined by the grinding tool 16 to a desired taper.

Figure 4:
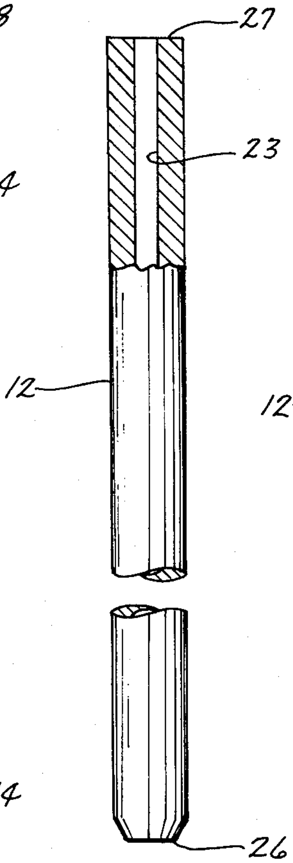
FIG. 4 is a foreshortened side elevational view of the handle member of the needle unit with a part broken away and shown in section.

The handle member 12 (FIG. 4) is of a tubular construction and is composed of a stainless steel tubing which may be nickel plated. The handle member has an axial bore 23 with a diameter slightly greater than the diameter of the needle member 11 to provide for the telescopic mounting thereof in a close tolerance relation about the working end 24 of the needle member. The outer edge of the inner end face 26 of the handle member 12 is of a beveled contour. The handle member 12 is mounted over its complete length about the working end 24 of the needle member 11, with the outer end face 27 thereof substantially flush with, or in the plane of the terminal face 28 at such working end.

Figure 5:
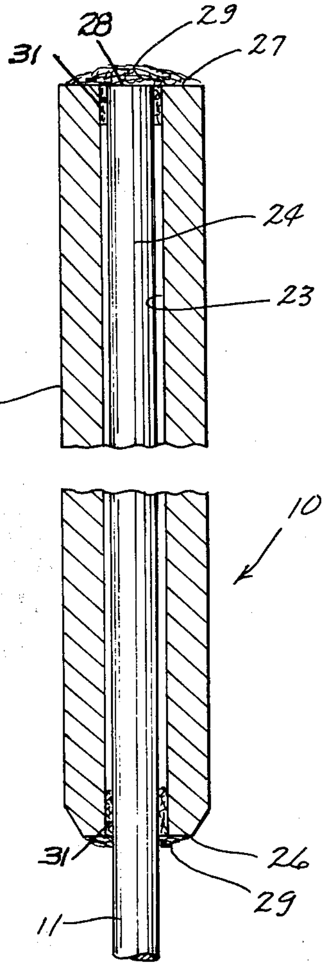
FIG. 5 is an enlarged detailed sectional view taken on line 5—5 in FIG. 2.

As best appears in FIG. 5, the handle member 12 and needle member 11 are rigidly secured together by applying a silver solder 29 in a covering relation with each end face 26 and 27 and within the bore 23 adjacent each end face, as indicated at 31. The solder 29 is formed with a generally dome shape to facilitate handling and sterilization of the needle unit.

In one embodiment of the invention the needle member 11 has a diameter of 0.014 inches, with the tapered section 14 having an over-all length of one-eighth of an inch and a taper or inclination of 4° relative to the axis of the needle member. In this embodiment the handle member 12 has an outer diameter of 0.050 inches, and an inner diameter of 0.033 inches. With a handle length of 1¼ inches, the needle member 11 may be varied in length from 2¼ inches to about 4¼ inches.

In use, the needle unit 10 (FIG. 1) has the handle member 12 held between the middle finger 32 and thumb 33 of a hand 34 at a position such that the index finger 36 is conveniently manipulated to tap the handle of the needle for insertion of the operating end 13 within a designated body portion of a patient. Due to the flexibility of the needle member 11 it may be necessary at times to position the needle member within a guide tube (not shown) for limiting the bending movement of the needle member during initiation of body insertion of the operating end 13.

Figure 9:
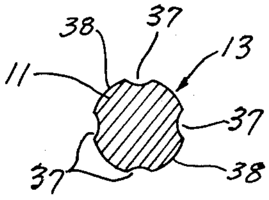
FIG. 9 is a sectional view on line 9—9 of FIG. 8.
Figure 8:
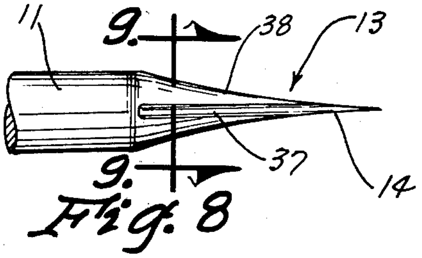
FIG. 8 is an exaggerated showing of the peripheral contour of the pointed end of the needle member of this invention.

By virtue of the machining of the needle point 14 axially of the needle member 11 any tool marks made by the grinding tool 16 will also extend axially of the needle member, as indicated at 37 in FIGS. 8 and 9. Insertion of the needle member within the body of a patient thus takes place with a minimum of pain since the initial puncture made by the 4° angle is small and the puncture thereafter is continuously and smoothly expanded as the needle member is inserted. This is for the reason that the surface of the markings 37 and the intervening circumferentially spaced surfaces 38 are similarly tapered and maintain a continuous engagement with the side wall of the puncture.

Figure 7:
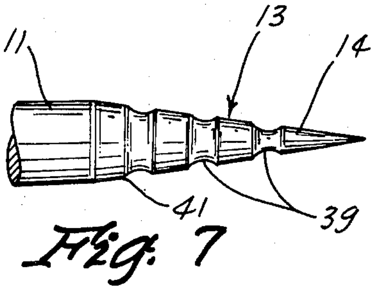
FIG. 7 is an exaggerated showing of the peripheral contour of the pointed end of presently available commercial type acupuncture needle members.

In contrast, when the tool markings extend circumferentially about the needle point 14, as shown at 39 in FIG. 7, they form recessed sections of different diameters spaced axially of the needle point 14. On insertion of the needle member 11, therefore, the side wall of the puncture is successively engaged by the trailing side 41 of each groove marking 39 so that expansion of the side wall of the puncture takes place in successive steps thereby causing unnecessary pain to a patient. In other words, the trailing side edges 41 tend to hook the side wall of the puncture as they enter the puncture. Importantly, the needle point is weakened in cross section at the markings 39 so that a portion of the point frequently breaks off at a marking 39. The broken portion remains unnoticed within the body of the patient due to its stainless steel construction and acceptance by the body without festering or soreness.

Although the invention has been described with respect to a preferred embodiment thereof, it is to be understood that it is not to be so limited since changes and modifications can be made therein which are within the full intended scope of this invention as defined by the appended claims.

I claim:

1. An acupuncture needle unit comprising:

a. an elongated flexible needle member composed of a stainless steel material and having a working end section and a body insertible end section formed with a pointed terminal portion, b. a tubular handle member having an axial bore therein of a size to telescopically receive therein said working end section over substantially the full length of said handle member, and c. means for rigidly securing together said handle member and working end section, d. said pointed terminal portion having an angle of not greater than about 4° relative to the longitudinal axis of the needle member and a peripheral surface having only axially extended tool markings thereon so as to have continuous engagement with the side wall of a puncture formed thereby.

* * * * *